(12) United States Patent
Li et al.

(10) Patent No.: US 12,256,904 B1
(45) Date of Patent: Mar. 25, 2025

(54) INSPECTION DEVICE WITH DISPLAY SCREEN

(71) Applicant: Zhengzhong Li, Shaoyang (CN)

(72) Inventors: Zhengzhong Li, Shaoyang (CN); Wenming Li, Shaoyang (CN)

( * ) Notice: Subject to any disclaimer, the term of this patent is extended or adjusted under 35 U.S.C. 154(b) by 0 days.

(21) Appl. No.: 18/812,322

(22) Filed: Aug. 22, 2024

(30) Foreign Application Priority Data

Apr. 28, 2024 (CN) .......................... 202420920604.7

(51) Int. Cl.
*A61B 1/227* (2006.01)
*A61B 1/00* (2006.01)
*A61F 11/00* (2022.01)

(52) U.S. Cl.
CPC .......... *A61B 1/227* (2013.01); *A61B 1/00048* (2013.01); *A61F 11/006* (2013.01)

(58) Field of Classification Search
CPC ....... A61B 1/227; A61B 1/267; A61B 1/2673; A61B 1/04; A61B 1/042; A61B 1/05; A61B 1/051; A61B 1/053; A61B 1/055; Y10T 403/32327; Y10T 403/32336; F16M 2200/021; F16M 2200/024
USPC ......................................................... 600/200
See application file for complete search history.

(56) References Cited

U.S. PATENT DOCUMENTS

| | | | | |
|---|---|---|---|---|
| 5,277,438 A * | 1/1994 | Chuang | ................... | A61H 3/04 280/42 |
| 5,442,831 A * | 8/1995 | Yamada | ............... | A46B 5/0083 403/92 |
| 6,220,125 B1 * | 4/2001 | Lan | ........................ | B25G 1/063 403/93 |
| 6,364,562 B1 * | 4/2002 | Tung | ...................... | A45B 17/00 403/96 |
| 7,171,875 B2 * | 2/2007 | Hu | ......................... | B25G 1/063 81/177.8 |
| 7,281,591 B2 * | 10/2007 | Bone | ...................... | H01R 35/02 173/171 |
| 2003/0195390 A1 * | 10/2003 | Graumann | ......... | A61B 1/00052 600/188 |
| 2004/0249244 A1 * | 12/2004 | Koda | .................... | A61F 11/006 600/200 |

(Continued)

FOREIGN PATENT DOCUMENTS

| CN | 110960194 A | 4/2020 |
|---|---|---|
| CN | 212118105 U | 12/2020 |

(Continued)

*Primary Examiner* — Jan Christopher L Merene

(57) ABSTRACT

An inspection device with a display screen relates to the technical field of care tools. The inspection device comprises: a handle internally provided with a control circuit board; a display module assembled at one end of the handle, wherein a display screen electrically connected to the control circuit board is arranged on one side of the display module; and an image acquisition module assembled at one side of the display module far away from the display screen and electrically connected to the control circuit board; wherein the display module is configured to display an image acquired by the image acquisition module. The display module is rotatably assembled at one end of the handle; and a channel which is communicated with the handle and the display module and is configured for a flexible circuit board to pass through is formed in the rotating seat.

9 Claims, 8 Drawing Sheets

(56) References Cited

U.S. PATENT DOCUMENTS

| | | | | |
|---|---|---|---|---|
| 2010/0095969 A1* | 4/2010 | Schwartz | ........... | A61B 1/00052 |
| | | | | 128/207.14 |
| 2011/0087073 A1* | 4/2011 | Huang | ............... | A61B 1/00052 |
| | | | | 345/87 |
| 2012/0071725 A1* | 3/2012 | Plevnik | .............. | A61B 1/00052 |
| | | | | 600/188 |
| 2012/0088976 A1* | 4/2012 | Shehadeh | .......... | A61B 1/00101 |
| | | | | 600/187 |
| 2013/0128223 A1* | 5/2013 | Wood | ................... | A61B 3/1208 |
| | | | | 351/246 |
| 2018/0080597 A1* | 3/2018 | Weldon | ................. | G06F 1/1615 |
| 2020/0094030 A1* | 3/2020 | Kim | ................... | A61B 1/00066 |
| 2023/0404384 A1* | 12/2023 | Siebenhaar | ........ | A61B 1/00066 |

FOREIGN PATENT DOCUMENTS

| CN | 213216835 U | 5/2021 |
|---|---|---|
| CN | 113080860 B | 11/2022 |
| CN | 218547505 U | 2/2023 |

\* cited by examiner

INSPECTION DEVICE WITH DISPLAY SCREEN

CROSS-REFERENCE TO RELATED APPLICATIONS

The application claims priority of Chinese patent application CN2024209206047, filed on Apr. 28, 2024, which is incorporated herein by reference in its entireties.

TECHNICAL FIELD

The present invention relates to the technical field of care tools, and in particular, to an inspection device with a display screen.

BACKGROUND

Currently, care tools with camera functions are widely used in daily production and life, such as a visual earpick and a pair of visual tweezers. Such care tools are not provided with a display screen and display the photographed content by a terminal device. For example, Chinese Patent Application Publication No. CN219516806U discloses a multipurpose visual earpick. Although this multipurpose visual earpick can photograph the ear canal of a user, the photographed image can only be observed through a mobile terminal, which is inconvenient for the operator to use. Therefore, the improvement is urgently required to be made.

SUMMARY

In view of the defects and shortcomings in the prior art, the present invention aims to provide an inspection device with a display screen, which has the advantage of facilitating an operator to directly observe the photographed image from the display screen of the inspection device during operation.

To achieve the above objective, the present invention adopts the following technical solution: an inspection device with a display screen comprises:
  a handle internally provided with a control circuit board;
  a display module assembled at one end of the handle, wherein a display screen electrically connected to the control circuit board is arranged on one side of the display module; and
  an image acquisition module assembled at one side of the display module far away from the display screen and electrically connected to the control circuit board; wherein
  the display module is configured to display an image acquired by the image acquisition module;
  a rotating seat is rotatably assembled at one end of the handle, the display module is fixedly assembled on the rotating seat, an arc-shaped travel hole is formed at one end of the handle, and the rotating seat comprises: a rotating seat body rotatably assembled in the handle, and a fixing portion arranged on the rotating seat body, extending out of the arc-shaped travel hole and configured to fix and assemble with the display module; and the rotating seat moves in the arc-shaped travel hole to enable the display module and the handle rotate relatively.

Preferably, a retainer is provided in the handle, an outwardly protruding rotating shaft is provided on the rotating seat body, one end of the retainer close to the arc-shaped travel hole is provided with a rotating shaft hole corresponding to the rotating shaft, and the rotating seat body is rotatably assembled at one end of the retainer close to the arc-shaped travel hole by the rotating shaft.

Preferably, a positioning structure is arranged between the rotating seat and the handle, so that the rotating seat can be positioned at a set angle.

Preferably, the retainer is provided with an elastic protrusion positioned in the rotating shaft hole and protruding toward the center of the rotating shaft hole, a plurality of arc-shaped grooves corresponding to the elastic protrusion are continuously provided on an outer peripheral wall of the rotating shaft, and when the rotating seat body rotates to a set angle, the elastic protrusion is placed in one of the arc-shaped grooves.

Preferably, the retainer comprises: a retainer body, and a retainer buckle cover assembled on the retainer body and configured to cooperate with the retainer body to prevent the rotating seat body from falling off, a space for the rotating seat body to be rotated and assembled is reserved between the retainer body and the retainer buckle cover, the retainer body and the retainer buckle cover jointly define the rotating shaft hole, and the elastic protrusion is mounted in the retainer buckle cover.

Preferably, the rotation angle between the display module and the handle is 90°.

Preferably, a rotating seat is rotatably assembled at one end of the handle, the display module is fixedly assembled on the rotating seat, and a channel which is communicated with the handle and the display module and is configured for a flexible circuit board to pass through is formed in the rotating seat.

Preferably, the display screen is circular, the image acquisition module comprises a camera, and the display screen is arranged parallel to the camera.

Preferably, the image acquisition module further comprises a strip-shaped inspection head assembled at one side of the display module far away from the display screen, the camera is arranged in the inspection head, and one end of the inspection head far away from the display screen is configured to assemble a workpiece.

Preferably, the inspection head is strip-shaped.

Preferably, the workpiece is one of an earpick head and a pair of tweezers.

Preferably, the fixing portion comprises a rod body extending outward from the rotating seat body and a sleeve body arranged on one side of the rod body, the display module is provided with a screw mounting post, and the sleeve body is sleeved on the screw mounting post and locked by screws.

With the adoption of the above technical solution, the present invention has the following beneficial effects. In the present invention, the display module with the display screen is arranged at one end of the handle, and the image acquisition module is arranged at the other side of the display screen, so that an operator can directly observe the image acquired by the image acquisition module by the display screen during operation. This operation is more convenient compared with the operation of observing the image from a mobile terminal. In addition, since the image acquisition module is assembled at one side of the display module far away from the display screen, that is, the acquisition end of the image acquisition module is arranged parallel to the display screen, the image observed by an operator from the display screen is similar to the angle at which the operator directly views the observed position, and the operator can control the inspection device to operate more conveniently.

BRIEF DESCRIPTION OF DRAWINGS

To more clearly illustrate the technical solution in the embodiments of the present invention or in the prior art, the accompanying drawings required to be used in the description of the embodiments or the prior art are briefly introduced below. It is obvious that the accompanying drawings in the description below are only some embodiments of the present invention, and those of ordinary skill in the art can obtain other accompanying drawings according to these accompanying drawings without creative efforts.

- 100: handle; 110: control circuit board; 120: arc-shaped travel hole; 130: retainer; 130a: rotating shaft hole; 131: retainer body; 132: retainer buckle cover;
- 200: display module; 210: display screen; 220: screw mounting post;
- 300: image acquisition module; 310: inspection head; 320: camera;
- 400: rotating seat; 400a: channel; 410: rotating seat body; 411: rotating shaft; 412: arc-shaped groove; 420: fixing portion; 421: rod body; 422: sleeve body;
- 500: flexible circuit board; and
- 600: elastic protrusion.

DETAILED DESCRIPTION OF EMBODIMENTS

The present invention is further described in detail below in conjunction with the accompanying drawings.

This specific embodiment is merely an explanation of the present invention, but not a limitation of the present invention. After reading this specification, those skilled in the art can make non-creative modifications to this embodiment based on a requirement, and these modifications are all protected by the Patent Law as long as they are within the scope of the claims of the present invention.

Figure 1:
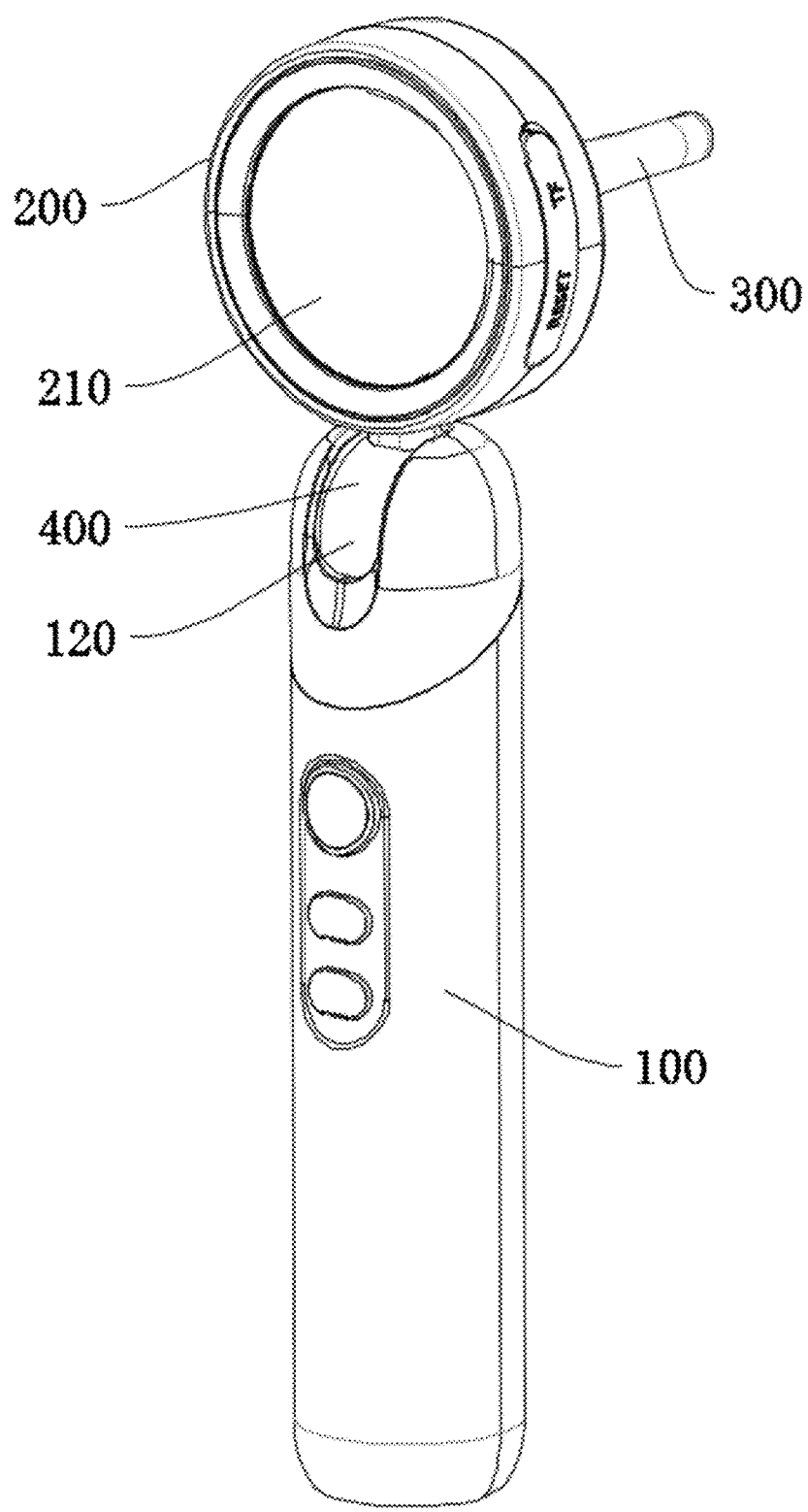
FIG. 1 is a schematic diagram of a structure of an inspection device.
Figure 2:
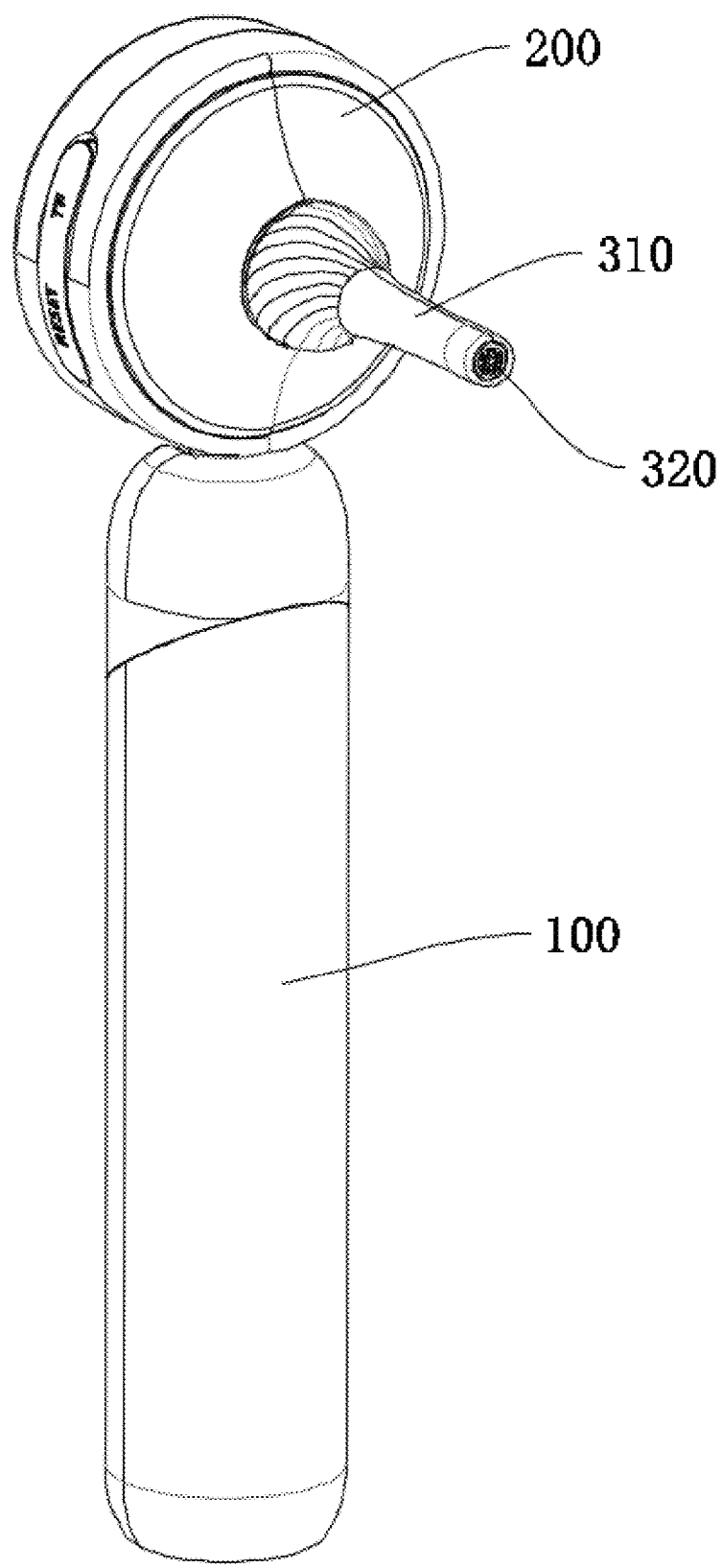
FIG. 2 is a schematic diagram of a structure of an inspection device from another perspective.

This embodiment relates to an inspection device with a display screen. Referring to FIGS. 1 to 2, the inspection device comprises: a handle 100, a display module 200 and an image acquisition module 300.

Referring to FIGS. 1 to 4, a control circuit board 110 is arranged in the handle 100. The display module 200 is assembled at one end of the handle 100, and a display screen 210 electrically connected to the control circuit board 110 is arranged at one side of the display module 200. The image acquisition module 300 is arranged at one side of the display module 200 far away from the display screen 210, and is electrically connected to the control circuit board 110. The display module 200 is configured to display an image acquired by the image acquisition module 300.

Specifically, in this embodiment, the image acquisition module 300 sends the acquired image information to the control circuit board 110, the control circuit board 110 performs image processing after receiving the image information, and sends the processed information to the display module 200, and finally the display screen 210 of the display module 200 displays the processed image.

The display module 200 with the display screen 210 is arranged at one end of the handle 100, and the image acquisition module 300 is arranged at the other side of the display screen 210, so that an operator can directly observe the image acquired by the image acquisition module 300 by the display screen 210 during operation. This operation is more convenient compared with the operation of observing the image from a mobile terminal. In addition, since the image acquisition module 300 is assembled at one side of the display module 200 far away from the display screen 210, that is, the acquisition end of the image acquisition module 300 is arranged parallel to the display screen 210, the image observed by an operator from the display screen 210 is similar to the angle at which the operator directly views the observed position, and the operator can control the inspection device to operate more conveniently.

Figure 3:
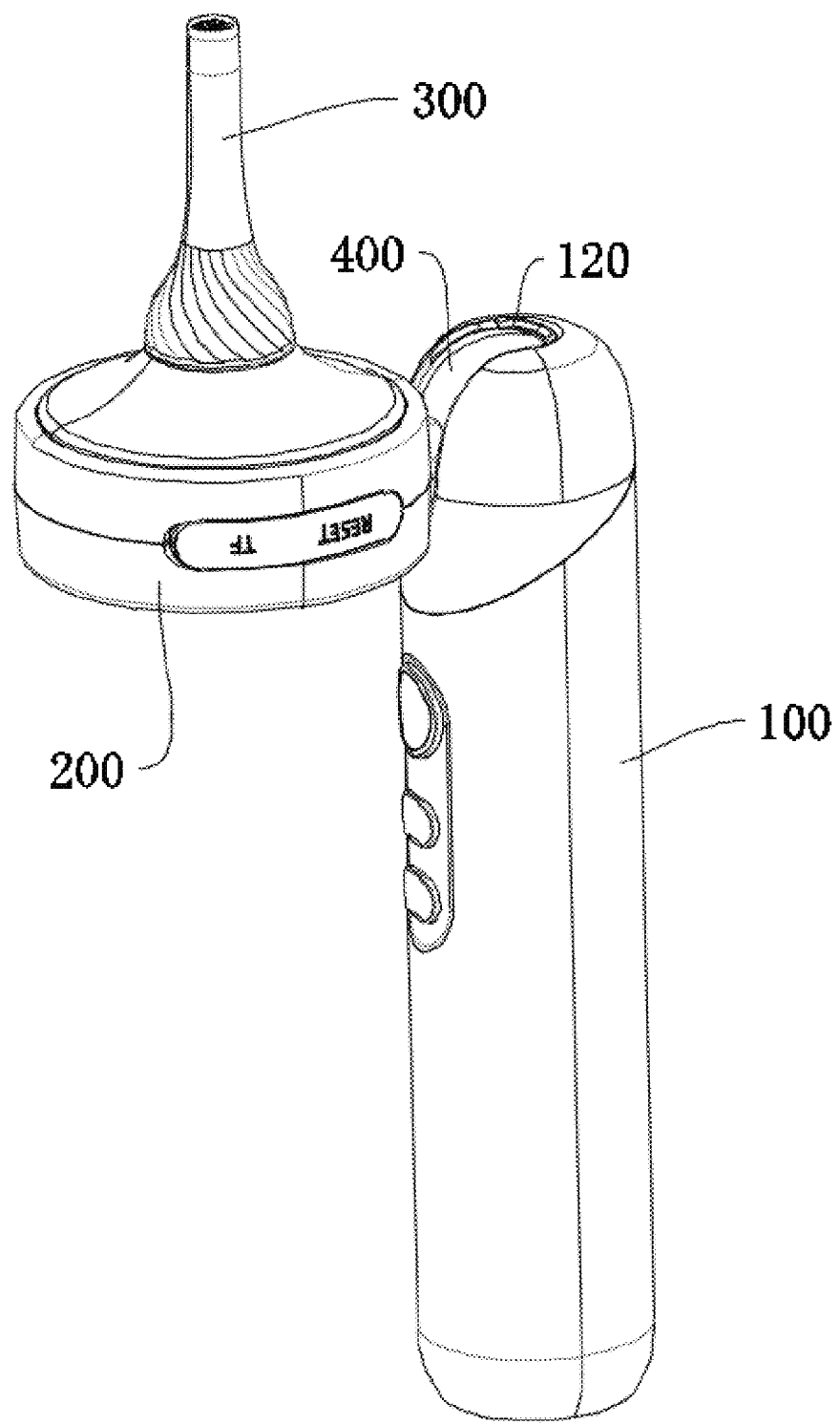
FIG. 3 is a schematic diagram of a structure of an inspection device, in which a display module is rotated to another angle.

In this embodiment, referring to FIGS. 1 to 3, display module 200 is rotatably assembled at one end of the handle 100. When the operator uses the inspection device, the display module 200 can be rotated relative to the handle 100 based on actual conditions, so that the optimal use angle can be adjusted, which is convenient for operation and observation. In a specific embodiment, taking the inspection device standing on the ground as an example, the rotation of the display module 200 is vertical, and the rotation plane of the display module 200 is perpendicular to the display screen 210. In other embodiments, the display module 200 may also be rotated in other directions relative to handle 100.

In this embodiment, referring to FIGS. 3 to 6, a rotating seat 400 is rotatably assembled at one end of the handle 100, and the display module 200 is fixedly assembled on the rotating seat 400. The rotating seat 400 is arranged between the handle 100 and the display module 200 as a rotating connector, and a channel 400a which is communicated with the handle 100 and the display module 200 is arranged in the rotating seat 400, so that the flexible circuit board 500 can pass through the channel 400a to electrically connect the control circuit board 110 in the handle 100 and the circuit board of the display screen 210. The flexible circuit board 500 is hidden in the rotating seat 400, which is safe and aesthetic. Since the flexible circuit board 500 is flexible, the rotation of the rotating seat 400 does not affect the electrical connection between the control circuit board 110 and the circuit board of the display screen 210.

Referring to FIGS. 3 to 4 and 6 to 8, an arc-shaped travel hole 120 is formed at one end of the handle 100. The rotating seat 400 comprises: a rotating seat body 410 rotatably assembled in the handle 100, and a fixing portion 420 arranged on the rotating seat body 410, extending out of the arc-shaped travel hole 120 and configured to fix and assemble with the display module 200.

Figure 4:
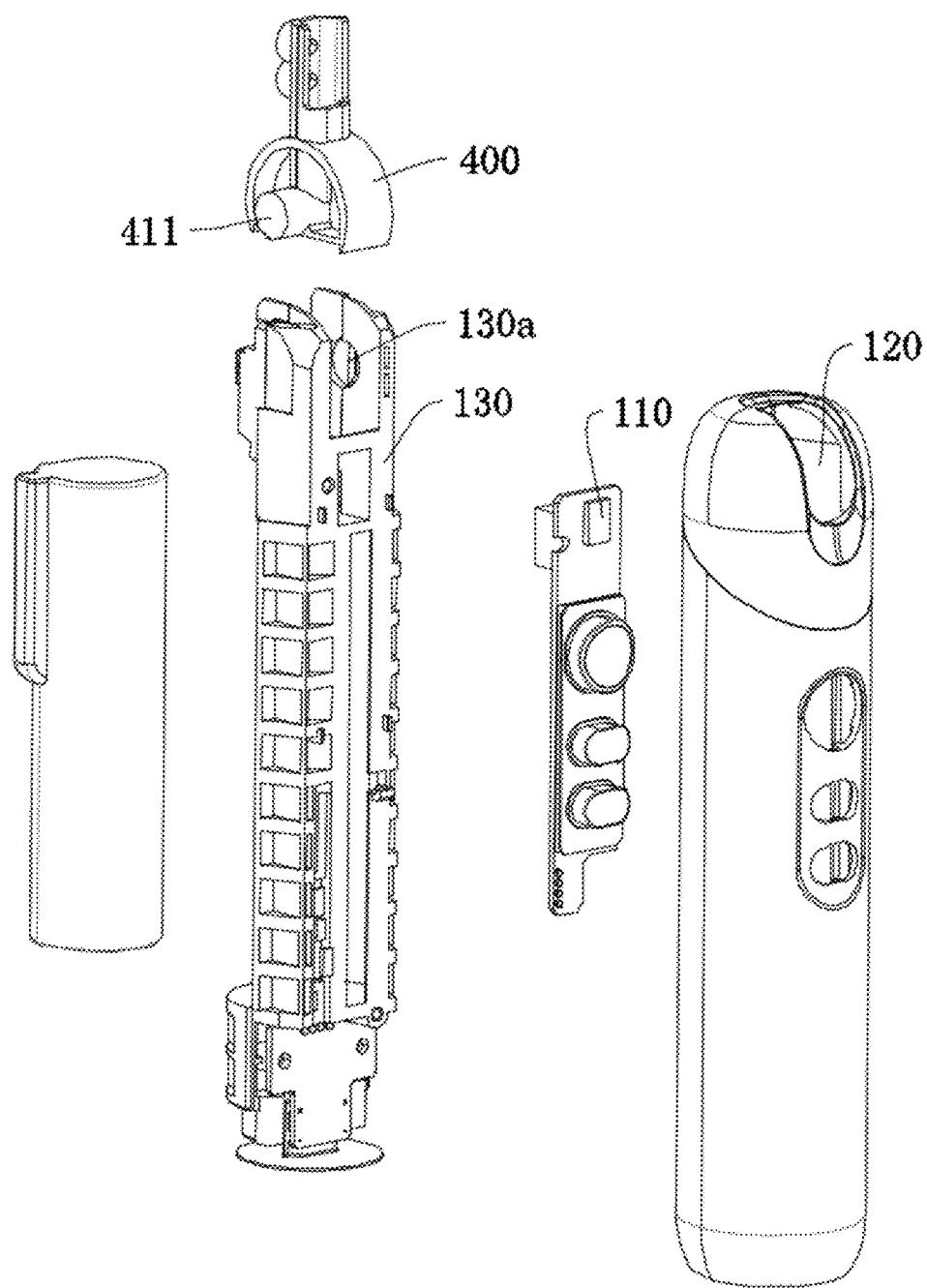
FIG. 4 is an exploded schematic diagram of structures of a handle and a rotating seat.
Figure 5:
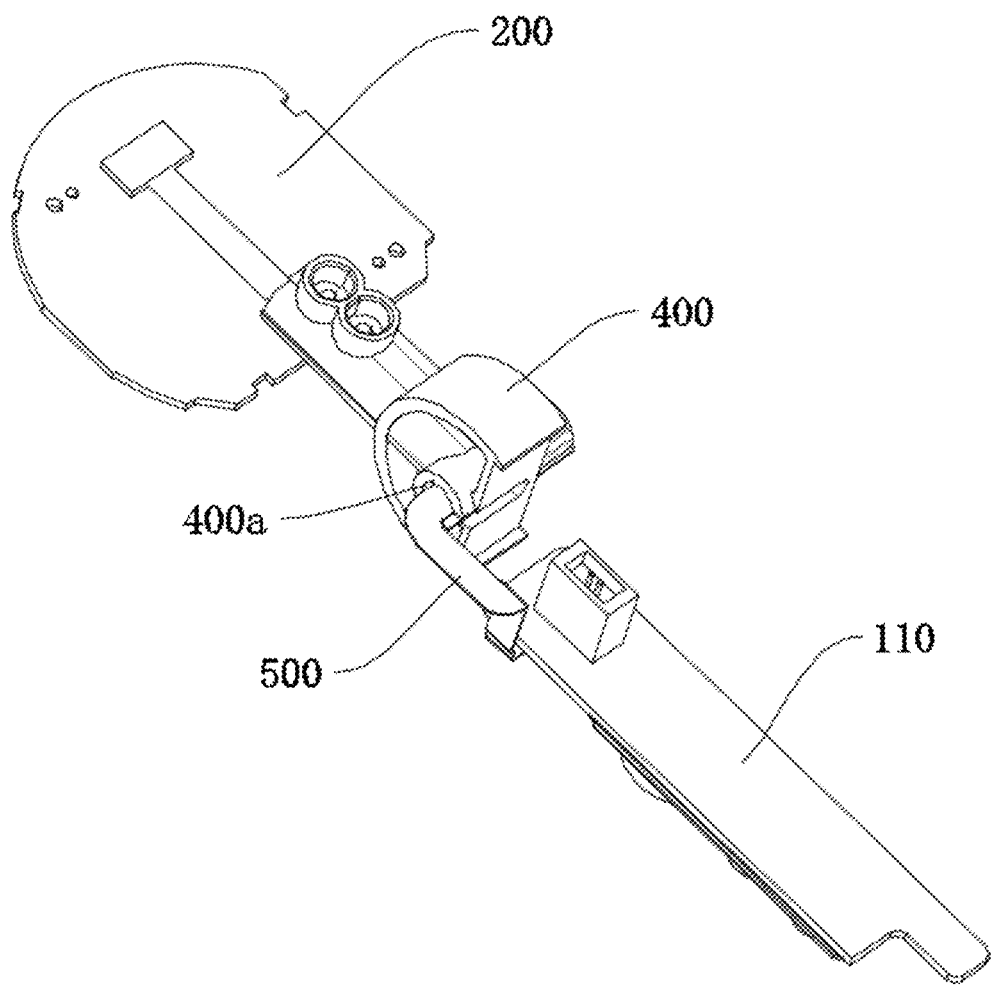
FIG. 5 is a schematic diagram of a structure of a flexible circuit board passing through a rotating seat.
Figure 7:
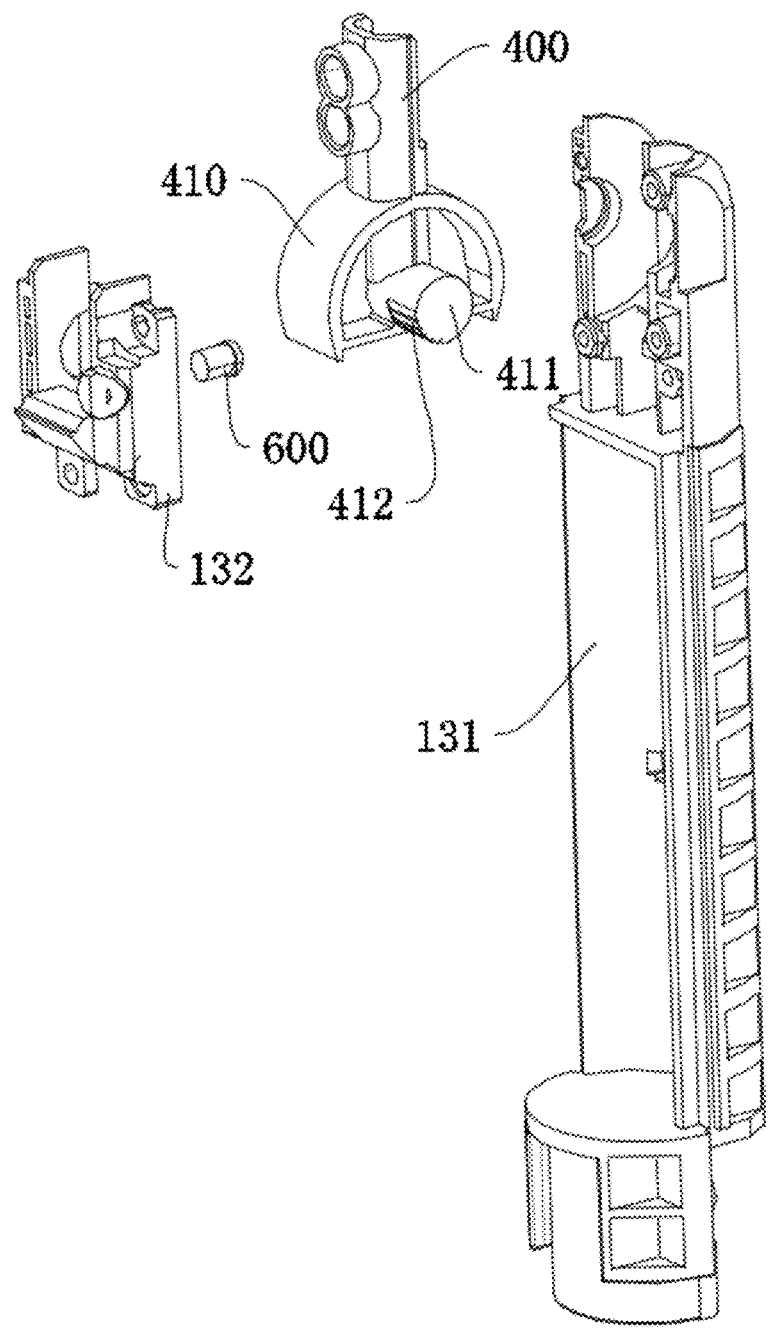
FIG. 7 is a schematic diagram of structures of a retainer, a rotating seat and an elastic protrusion.
Figure 8:
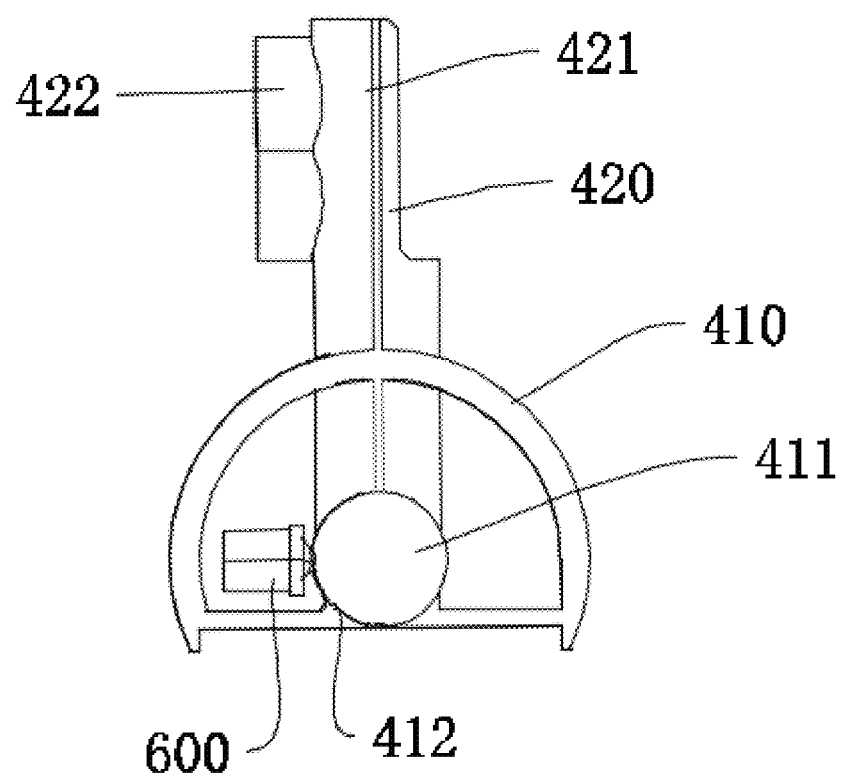
FIG. 8 is a schematic diagram of structures of a rotating seat and an elastic protrusion.

In this embodiment, referring to FIGS. 4 and 7, a retainer 130 is provided in the handle 100, and the rotating seat body 410 is rotatably assembled at one end of the retainer 130 close to the arc-shaped travel hole 120.

Figure 6:
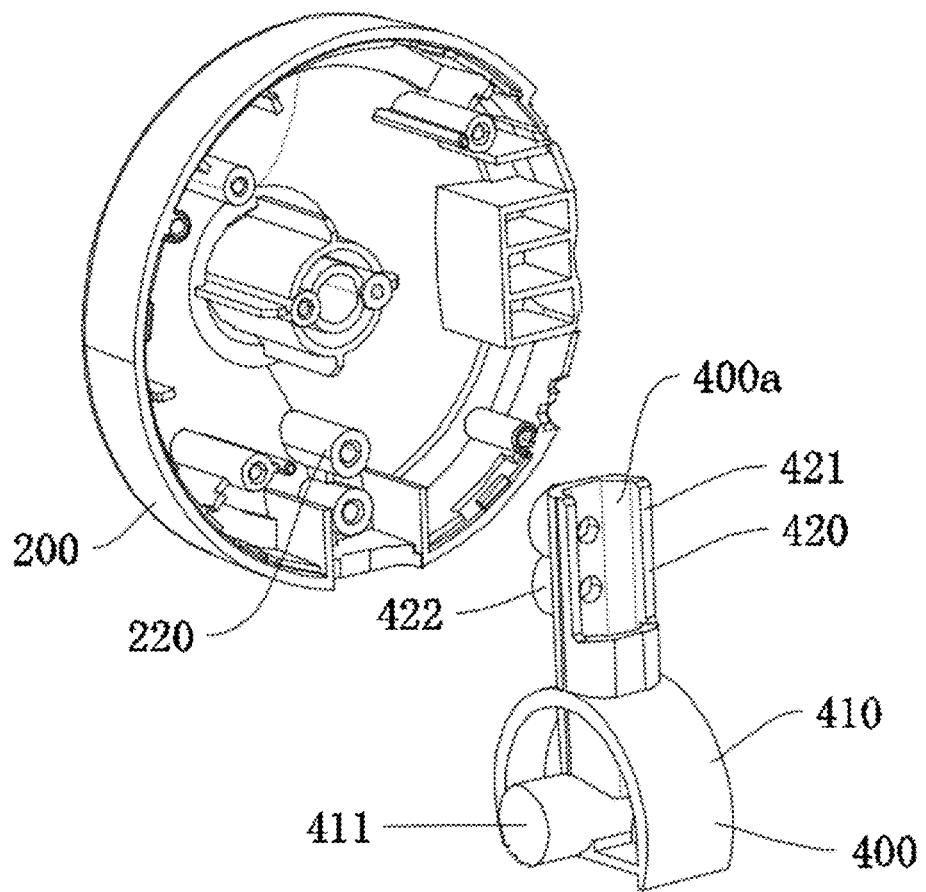
FIG. 6 is a schematic diagram of structures of a display module and a rotating seat.

In this embodiment, referring to FIG. 6, the fixing portion 420 of the rotating seat 400 comprises a rod body 421 extending outward from the rotating seat body 410 and a sleeve body 422 arranged on one side of the rod body 421.

The sleeve body 422 is sleeved on the screw mounting post 220 of the display module 200, and the sleeve body 422 is locked on the screw mounting post 220 by a screw, so that the fixed connection between the rotating seat 400 and the display module 200 is achieved. In other embodiments, the fixing portion 420 of the rotating seat 400 may be configured as other structures.

Referring to FIGS. 4 and 6 to 8, an outwardly protruding rotating shaft 411 is provided on the rotating seat body 410, one end of the retainer 130 close to the arc-shaped travel hole 120 is provided with a rotating shaft hole 130a corresponding to the rotating shaft 411. The rotating shaft 411 is rotatably assembled in the rotating shaft hole 130a, and the entire rotating seat 400 can rotate around the rotating shaft hole 130a. To position the display module 200 at a plurality of angles, the retainer 130 is provided with an elastic protrusion 600 positioned in the rotating shaft hole 130a and protruding toward the center of the rotating shaft hole 130a, a plurality of arc-shaped grooves 412 corresponding to the elastic protrusion 600 are continuously provided on an outer peripheral wall of the rotating shaft 411. When the rotating seat body 410 rotates to a set angle, the elastic protrusion 600 is placed in one of the arc-shaped grooves 412, so that the angle positioning of the rotating seat body 410, namely the angle positioning of the display module 200, is achieved. When the angle of the display module 200 is changed, the display module 200 needs to be rotated with force; in this case, the elastic protrusion 600 is squeezed and in a compressed state. When the display module 200 is rotated to the set angle, the elastic protrusion 600 is aligned to another arc-shaped groove 412; in this case, the elastic protrusion 600 is no longer squeezed, and the elastic protrusion 600 extends outward under the action of the rebound force and presses against the arc-shaped groove 412, thereby achieving the angle positioning of the display module 200.

Referring to FIG. 7, the retainer 130 comprises: a retainer body 131, and a retainer buckle cover 132 assembled on the retainer body 131 and configured to cooperate with the retainer body 131 to prevent the rotating seat body 410 from falling off. A space for the rotating seat body 410 to be rotated and assembled is reserved between the retainer body 131 and the retainer buckle cover 132, the retainer body 131 and the retainer buckle cover 132 jointly define the rotating shaft hole 130a, that is, the retainer body 131 and the retainer buckle cover 132 each have half of the rotating shaft hole 130a, and when the two are combined, a complete rotating shaft hole 130a is formed. In this embodiment, the elastic protrusion 600 is mounted in the retainer buckle cover 132. During assembly, the rotating seat 400 is firstly mounted on the retainer body 131, the elastic protrusion 600 is mounted in the retainer buckle cover 132, and then the retainer buckle cover 132 is covered. In this case, the rotating seat 400 is limited in the retainer 130, the rotating shaft 411 of the rotating seat 400 is positioned in the rotating shaft hole 130a, and the elastic protrusion 600 is aligned to the arc-shaped groove 412.

In other embodiments, other types of positioning structures may be arranged between the rotating seat 400 and the handle 100, so that the rotating seat 400 can be positioned at a set angle.

In this embodiment, referring to FIGS. 1 to 2, the image acquisition module 300 comprises: a strip-shaped inspection head 310 assembled at one side of the display module 200 far away from the display screen 210, and a camera 320 arranged in the inspection head 310 and having a photographing end facing one side far away from the display screen 210. One end of the inspection head 310 far away from the display screen 210 is configured to assemble a workpiece (not shown). The workpiece may be an earpick head, a pair of tweezers and the like. When the workpiece is the earpick head, the inspection device is the visual earpick, and when the workpiece is a pair of tweezers, the inspection device is the visual tweezers. In a preferred embodiment, the workpiece is detachably connected to one end of the inspection head 310 far away from the display screen 210, so that the user can replace different workpieces based on a requirement.

In this embodiment, the display module 200 is in a shape of a round pie, the display screen 210 is in a shape of a circle, and a TF card slot is arranged on the display module 200. The handle 100 is in a shape of a round rod. The handle 100 is further provided with a battery, a charging port, a plurality of function buttons, and the like.

The principle of the present invention is substantially as follows: the display module 200 with the display screen 210 is arranged at one end of the handle 100, and the image acquisition module 300 is arranged at the other side of the display screen 210, so that an operator can directly observe the image acquired by the image acquisition module 300 by the display screen 210 during operation. This operation is more convenient compared with the operation of observing the image from a mobile terminal. In addition, since the image acquisition module 300 is assembled at one side of the display module 200 far away from the display screen 210, that is, the acquisition end of the image acquisition module 300 is arranged parallel to the display screen 210, the image observed by an operator from the display screen 210 is similar to the angle at which the operator directly views the observed position, and the operator can control the inspection device to operate more conveniently.

The above description is only intended to illustrate the technical solution of the present invention and not to limit the present invention, and other modifications or equivalent substitutions made by those skilled in the art to the technical solution of the present invention should be covered by the scope of the claims of the present invention without departing from the spirit and scope of the technical solution of the present invention.

What is claimed is:
1. An inspection device with a display screen, comprising:
   a handle (100) internally provided with a control circuit board (110);
   a display module (200) assembled at one end of the handle (100), wherein the display screen (210) electrically connected to the control circuit board (110) is arranged on one side of the display module (200); and
   an image acquisition module (300) assembled at a second side of the display module (200) away from the display screen (210), wherein the image acquisition module (300) is electrically connected to the control circuit board (110); wherein
   the display module (200) is configured to display an image acquired by the image acquisition module (300);
   a rotating seat (400) is rotatably assembled at one end of the handle (100), the display module (200) is fixedly assembled on the rotating seat (400), an arc-shaped travel hole (120) is formed at one end of the handle (100), and the rotating seat (400) comprises: a rotating seat body (410) rotatably assembled in the handle (100), and a fixing portion (420) arranged on the rotating seat body (410), extending out of the arc-shaped travel hole (120) and configured to fix and assemble with the display module (200); and the rotat- ing seat (400) moves in the arc-shaped travel hole (120) to enable the display module (200) and the handle (100) rotate relatively;

wherein a retainer (130) is provided in the handle (100), an outwardly protruding rotating shaft (411) is provided on the rotating seat body (410), one end of the retainer (130) close to the arc-shaped travel hole (120) is provided with a rotating shaft hole (130*a*) corresponding to the rotating shaft (411), and the rotating seat body (410) is rotatably assembled at one end of the retainer (130) close to the arc-shaped travel hole (120) by the rotating shaft (411);

wherein the retainer (130) is provided with an elastic protrusion (600) positioned in the rotating shaft hole (130*a*) and protruding toward the center of the rotating shaft hole (130*a*);

wherein the retainer (130) comprises: a retainer body (131), and a retainer buckle cover (132) assembled on the retainer body (131) and configured to cooperate with the retainer body (131) to prevent the rotating seat body (410) from falling off, a space for the rotating seat body (410) to be rotated and assembled is reserved between the retainer body (131) and the retainer buckle cover (132), the retainer body (131) and the retainer buckle cover (132) jointly define the rotating shaft hole (130*a*), and the elastic protrusion (600) is mounted in the retainer buckle cover (132).

2. The inspection device with the display screen according to claim 1, wherein a positioning structure is arranged between the rotating seat (400) and the handle (100), so that the rotating seat (400) can be positioned at a set angle.

3. The inspection device with the display screen according to claim 2, wherein a plurality of arc-shaped grooves (412) corresponding to the elastic protrusion (600) are continuously provided on an outer peripheral wall of the rotating shaft (411), and when the rotating seat body (410) rotates to the set angle, the elastic protrusion (600) is placed in one of the arc-shaped grooves (412).

4. The inspection device with the display screen according to claim 2, wherein a rotation angle between the display module (200) and the handle (100) is 90°.

5. The inspection device with the display screen according to claim 1, wherein a channel (400*a*) communicated with the handle (100) and the display module (200) and allowing a flexible circuit board (500) to pass through is formed in the rotating seat (400).

6. The inspection device with the display screen according to claim 1, wherein the display screen (210) is circular, the image acquisition module (300) comprises a camera (320), and the display screen (210) is arranged parallel to the camera (320).

7. The inspection device with the display screen according to claim 6, wherein the image acquisition module (300) further comprises an inspection head (310) assembled at the second side of the display module (200) away from the display screen (210), the camera (320) is arranged in the inspection head (310).

8. The inspection device with the display screen according to claim 7, wherein the inspection head (310) is strip-shaped.

9. The inspection device with the display screen according to claim 1, wherein the fixing portion (420) comprises a rod body (421) extending outward from the rotating seat body (410) and a sleeve body (422) arranged on one side of the rod body (421), the display module (200) is provided with a screw mounting post (220), and the sleeve body (422) is sleeved on the screw mounting post (220) and locked by screws.

* * * * *